United States Patent
Hayes

(10) Patent No.: US 11,464,421 B2
(45) Date of Patent: Oct. 11, 2022

(54) OPTICAL CONNECTOR FOR OPTICALLY CONNECTING A PROXIMAL OPTICAL FIBER TO THE DISTAL OPTICAL FIBER OF A GUIDEWIRE

(71) Applicant: Lake Region Manufacturing, Inc., Chaska, MN (US)

(72) Inventor: John Michael Hayes, Cork (IE)

(73) Assignee: Lake Region Manufacturing, Inc., Chaska, MN (US)

( * ) Notice: Subject to any disclaimer, the term of this patent is extended or adjusted under 35 U.S.C. 154(b) by 513 days.

(21) Appl. No.: 16/523,121

(22) Filed: Jul. 26, 2019

(65) Prior Publication Data

US 2020/0029855 A1 Jan. 30, 2020

Related U.S. Application Data

(60) Provisional application No. 62/711,131, filed on Jul. 27, 2018.

(51) Int. Cl.
*A61B 5/06* (2006.01)
*A61B 5/026* (2006.01)
*A61B 5/00* (2006.01)

(52) U.S. Cl.
CPC ............ *A61B 5/065* (2013.01); *A61B 5/0261* (2013.01); *A61B 5/6851* (2013.01); *A61B 2562/146* (2013.01)

(58) Field of Classification Search
CPC .. A61B 5/6851; A61B 2562/146; A61B 5/065
See application file for complete search history.

(56) References Cited

U.S. PATENT DOCUMENTS

| | | |
|---|---|---|
| 4,763,980 A | 8/1988 | Gerber et al. |
| 4,886,062 A | 12/1989 | Wiktor |
| 5,439,000 A | 8/1995 | Gunderson et al. |
| | (Continued) | |

FOREIGN PATENT DOCUMENTS

| | | |
|---|---|---|
| EP | 0351240 A2 | 1/1990 |
| WO | 2012029013 | 3/2012 |

OTHER PUBLICATIONS

Extended European Search, Application No. 19188919.5, dated Dec. 11, 2019.

*Primary Examiner* — Oommen Jacob
(74) *Attorney, Agent, or Firm* — Michael F. Scalise

(57) ABSTRACT

A guidewire system comprises a guidewire supporting a distal ferrule in the proximal end of a guidewire lumen. The distal ferrule has a ferrule opening that is sized to snuggly receive the proximal end of a distal optical fiber with a distal portion of the distal optical fiber extending into the guidewire lumen. However, the proximal end of the distal optical fiber only occupies a distal portion of the opening in the distal ferrule, leaving a proximal portion of that opening unoccupied. That way, the distal end of a proximal optical fiber can be received into the unoccupied proximal portion of the opening in the distal ferrule to optically connect to the distal optical fiber. Having the proximal and distal optical fibers coaxially aligned in a common opening in a ferrule received in a guidewire ensures that the optical fibers are optically connected to each other in a precise manner so that light can be transmitted along them with minimal losses.

20 Claims, 6 Drawing Sheets

(56) References Cited

U.S. PATENT DOCUMENTS

| | | | |
|---|---|---|---|
| 5,872,879 A * | 2/1999 | Hamm | G02B 6/3604 |
| | | | 385/25 |
| 5,987,995 A | 11/1999 | Sawatari et al. | |
| 6,134,003 A | 10/2000 | Tearney et al. | |
| 6,263,133 B1 | 7/2001 | Hamm | |
| 6,445,939 B1 | 9/2002 | Swanson et al. | |
| 6,761,490 B2 * | 7/2004 | Wada | C03C 10/00 |
| | | | 385/68 |
| 6,868,736 B2 | 3/2005 | Sawatari et al. | |
| 7,736,301 B1 * | 6/2010 | Webler | G02B 6/3826 |
| | | | 600/125 |
| 8,345,238 B2 | 1/2013 | Yao | |
| 8,936,401 B2 * | 1/2015 | Belleville | G02B 6/381 |
| | | | 385/80 |
| 9,268,098 B2 | 2/2016 | Kat | |
| 9,405,078 B2 | 8/2016 | Belleville et al. | |
| 9,869,826 B1 | 1/2018 | Shang | |
| 2002/0146211 A1 * | 10/2002 | Stevens | G02B 6/3846 |
| | | | 385/61 |
| 2004/0034311 A1 | 2/2004 | Mihalcik | |
| 2009/0196554 A1 | 8/2009 | Irisawa | |
| 2010/0069721 A1 * | 3/2010 | Webler | A61B 1/00126 |
| | | | 600/182 |
| 2013/0051731 A1 * | 2/2013 | Belleville | G02B 6/381 |
| | | | 385/72 |
| 2014/0350414 A1 * | 11/2014 | Mcgowan | A61B 5/02154 |
| | | | 600/480 |
| 2015/0141843 A1 * | 5/2015 | Eberle | G01L 19/149 |
| | | | 600/478 |
| 2020/0029855 A1 * | 1/2020 | Hayes | A61B 5/0261 |

\* cited by examiner

OPTICAL CONNECTOR FOR OPTICALLY CONNECTING A PROXIMAL OPTICAL FIBER TO THE DISTAL OPTICAL FIBER OF A GUIDEWIRE

CROSS-REFERENCE TO RELATED APPLICATION

This application claims priority to U.S. Provisional Application Ser. No. 62/711,131, filed on Jul. 27, 2018.

BACKGROUND OF THE INVENTION

1. Field of the Invention

The present invention relates to the field of medical devices, and specifically to a guidewire system including a distal optical fiber extending at least part way along the length of an opening in the guidewire. An optical connector detachably connects the distal optic fiber to a proximal optical fiber. That way, after a diagnostic or therapeutic instrument, for example a catheter, has been moved along the guidewire to a point of interest in the vasculature of a patient, the optical connector provides for optically connecting the distal optical fiber to a proximal optical fiber. The proximal optical fiber in turn is connectable to a proximal interrogation system, for example an optical interrogation system comprising a light source, a light detector, and associate equipment.

In that respect, an optical fiber can be integrated into a guidewire to optically transfer information and power to and from the guidewire. But the guidewire must allow a diagnostic or therapeutic instrument, for example a catheter, to be loaded onto its proximal end so that the diagnostic or therapeutic instrument can travel over the guidewire to a point of interest in the vasculature of a patient. This means that an optical connector is needed for connecting a proximal optical fiber to the distal optical fiber supported by the guidewire. The optical connector must allow the guidewire and its distal optical fiber to be inserted into the patient's vasculature so that a catheter or other diagnostic or therapeutic instrument can be moved over the guidewire and into the vasculature. Then, with the diagnostic or therapeutic instrument received over the guidewire, the optical connector must enable the guidewire and its distal optical fiber to be optically connected to a proximal optical fiber. Also, the guidewire needs to be able to be inserted at any rotational angle without significant power loss across the optical connector.

An aspect of the present invention which is an improvement over a conventional guidewire supporting an optical fiber is that a distal ferrule is supported at the proximal end of the guidewire. The distal optical fiber resides in a distal portion of an opening extending through the distal ferrule, leaving a proximal portion of the distal ferrule opening unoccupied and free to receive the distal end of a proximal optical fiber. In that respect, the guidewire and the opening in its distal ferrule become the female part of the optical connector and the proximal optical fiber the male part. When the two optical fibers meet in the opening in the distal ferrule, they automatically self-align as the diameter of the opening through the distal ferrule supported by the guidewire is consistent throughout its length.

2. Prior Art

U.S. Pat. No. 8,936,401 to Belleville et al. describes a connector for optically connecting a guidewire mounted optical pressure sensor to an external pressure analyzer or a similar opto-electronic device. An alignment assembly comprises a distal ferrule that receives the proximal end of a guidewire. A distal optical fiber is centered in a lumen of the guidewire using only an adhesive or an overlay tubing with adhesive. A proximal ferrule supports a proximal optical fiber. The distal and proximal optical fibers are cut flush with the ends of their respective ferrules and polished. The proximal and distal ferrules are then aligned and held together using a split sleeve. Provided the proximal and distal ferrules are coaxially aligned with each other and that the exposed faces of the respective proximal and distal optical fibers are in intimate contact, an optical connection of the proximal and distal optical fibers is made with minimal light transmission losses.

However, Belleville et al. implicitly recognized the shortcoming of their optical connector when they acknowledged that an optical connection with minimal light transmission losses is obtained only if coaxial alignment of the two optical fibers is precise with their exposed faces being in intimate contact with each other. The problem is that the use of an adhesive or an overlay tubing, which is intended to reduce but not eliminate the adhesive, inherently introduces some degree of potential misalignment that is undesirable.

Therefore, there is a need for an optical connector that is easy to use for reliably optically connecting a distal optical fiber supported by a guidewire to a proximal optic fiber to transmit light along the optical fibers with minimal transmission losses. The present invention relates to guidewire systems comprising such an optical connector.

SUMMARY OF THE INVENTION

The present guidewire system overcomes the shortcomings of the prior art by supporting a distal ferrule in the proximal end of a guidewire lumen. The distal ferrule has a ferrule opening that is sized to snuggly receive the proximal end of a distal optical fiber with a distal portion of the distal optical fiber extending into the guidewire lumen. In the present invention, the proximal end of the distal optical fiber only occupies a distal portion of the opening in the distal ferrule, leaving a proximal portion of that opening unoccupied. That way, the distal end of a proximal optical fiber can be received into the unoccupied proximal portion of the opening in the distal ferrule to optically connect to the distal optical fiber. Having the proximal and distal optical fibers coaxially aligned in a common opening in a ferrule received in a guidewire ensures that the optical fibers are optically connected to each other in a precise manner so that light can be transmitted along them with minimal losses.

Another important aspect of the present invention is that the proximal optical fiber is supported in a proximal ferrule contained in the optical connector. A distal portion of the proximal optical fiber extends distally outwardly from the proximal ferrule. It is this extending portion of the proximal optical fiber that is received in the unoccupied proximal portion of the opening in the distal ferrule to contact the distal optical fiber. However, as the guidewire assembly including its distal ferrule supporting the distal optical fiber is moved proximally into the optical connector to mate with the proximal optical fiber, there is a concern that the relatively fragile optical fibers could be damaged when they contact each other. To help ensure that the optical fibers are not damaged, a spring is housed in the optical connector. The spring is preferably a coil spring and contacts the proximal ferrule opposite the extending distal portion of the proximal optical fiber. The spring provides a degree of biasing resistance that permits the proximal ferrule to translate proximally a relatively short distance to help absorb any potentially damaging force that might occur as the distal optical fiber moves into contact with the proximal optical fiber.

In that respect, the optical connector is where the distal and proximal optical fibers are optically connected and disconnected to and from each other. The optical connector of the present invention also provides for removably connecting a guidewire assembly to a proximal interrogation system, for example an optical interrogation system comprising a light source, a light detector, and associate equipment. However, the optical connector is not necessarily connected to the guidewire assembly as the guidewire is advanced into position within the vasculature. This allows for use of the guidewire assembly as a conventional guidewire for advancing a catheter or other diagnostic or therapeutic instrument into the vasculature. Then, with the guidewire in the desire position in the vasculature, the optical connector of the present invention provides for readily optically connecting a proximal optical fiber to the distal optical fiber of the guidewire assembly. That is with minimal loss in the transmitted light between the distal and proximal optical fibers.

These and other aspects of the present invention will become increasingly more apparent to those skilled in the art by reference to the following detailed description and to the appended drawings.

DETAILED DESCRIPTION OF THE PREFERRED EMBODIMENTS

Figure 1:
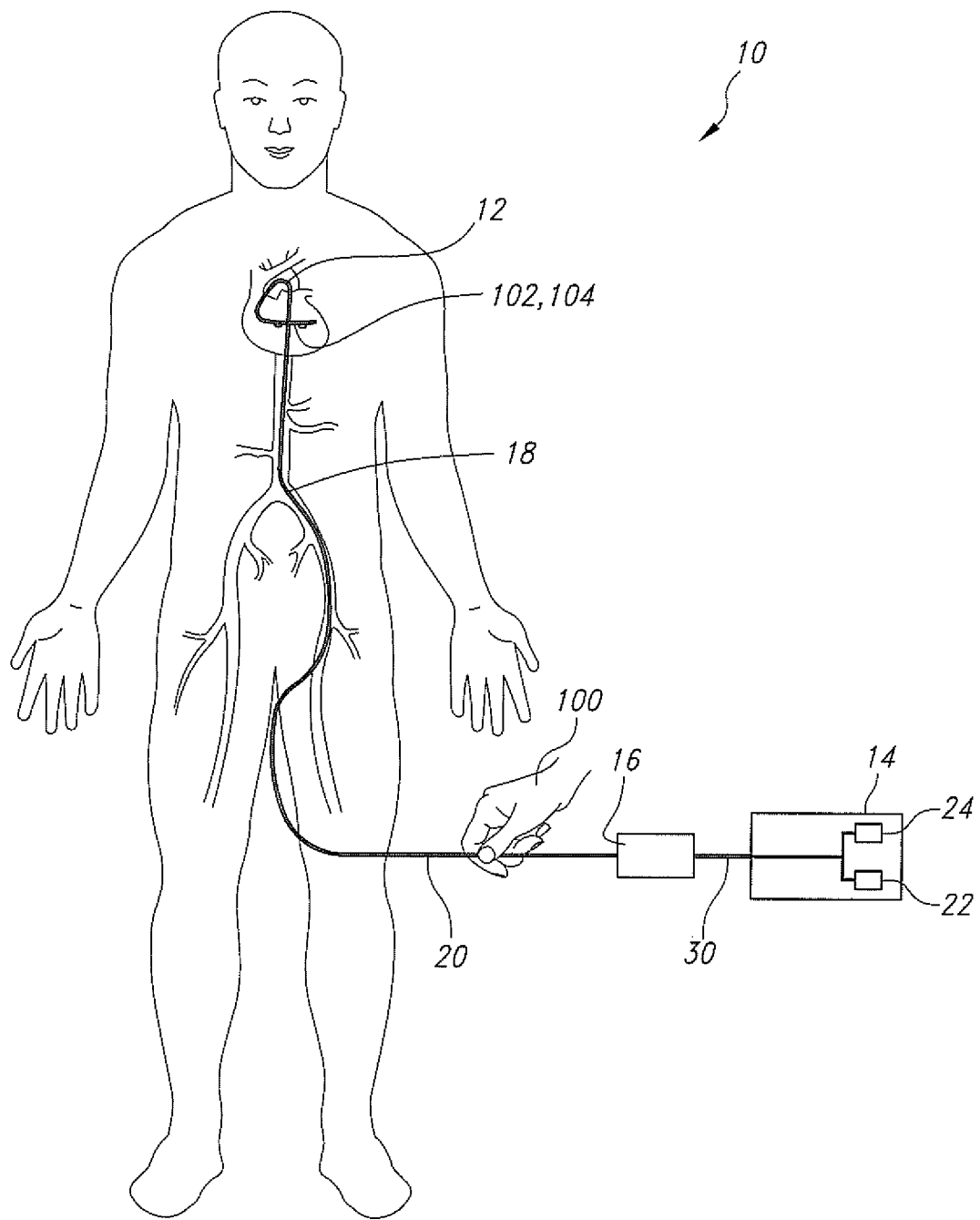
FIG. 1 is a schematic view of a catheter system 10 including a guidewire assembly 12 in its environment of use.

Turning now to the drawings, FIG. 1 is a schematic illustration of a guidewire system 10 including a guidewire housing a distal optical fiber for use in the collection of diagnostic or therapeutic information, for example temperature or pressure, during an angioplasty procedure, a stenting procedure, or a CTO (chronic total occlusion) procedure, and the like. In those exemplary procedures, the distal optical fiber can support one or more fiber Bragg grating sensors for obtaining a FFR measurement, a Fabry-Perot type sensor, or the distal optical fiber could couple light into the vasculature and then collect the resulting scattered light for diagnostic purposes. The guidewire system 10 can also deliver therapy to the patient through the vasculature.

The guidewire system 10 is comprised of three primary assemblies. They are a distal guidewire assembly 12, a proximal assembly 14 and an intermediate optical connector 16. The guidewire assembly 12 is comprised of a guidewire 18 and a distal optical fiber 20. The proximal assembly 14 is an interrogator system that can take many forms depending on the type of measurement device the distal optical fiber 20 is provided with. In any event, the proximal assembly 14 generally includes a light source 22 and a reflected light receiver 24, both connected to a proximal optical fiber 30. The optical connector 16 resides between and optically connects the distal optical fiber 20 of the distal guidewire assembly 12 to the proximal optical fiber 30 of the proximal assembly 14.

FIG. 1 is a schematic view illustrating an exemplary use of the guidewire system 10 in a fractional flow reserve (FFR) diagnostic procedure. In such a procedure, the distal guidewire assembly 12 enters the patient via Seldinger or another technique and is introduced into the vasculature. Under fluoroscopy or other imaging techniques, the guidewire assembly 12 is advanced by the physician or practitioner (represented by the depicted hand 100) to an affected region 102 of a vessel 104. The affected region 102 may be a lesion, occlusion or other abnormality within the vessel 104 causing restriction in blood flow therethrough. The guidewire assembly 12 is now positioned for moving a diagnostic or therapeutic instrument such as a catheter to the affected region 102.

FIGS. 2 to 5 illustrate the optical connector 16 in greater detail for optically connecting the distal guidewire assembly 12 to the proximal assembly 14. The distal guidewire assembly 12 is comprised of an elongate guidewire 18 extending from a guidewire proximal open end 32 to a guidewire distal end, preferably provided with an atraumatic tip (not shown). A lumen 34 extends through the guidewire 18 from the proximal open end 32 toward the distal end. Depending on the specific procedure for which the guidewire 18 is designed, the guidewire lumen 34 may or may not extend all the way to the distal atraumatic tip.

Figure 3:
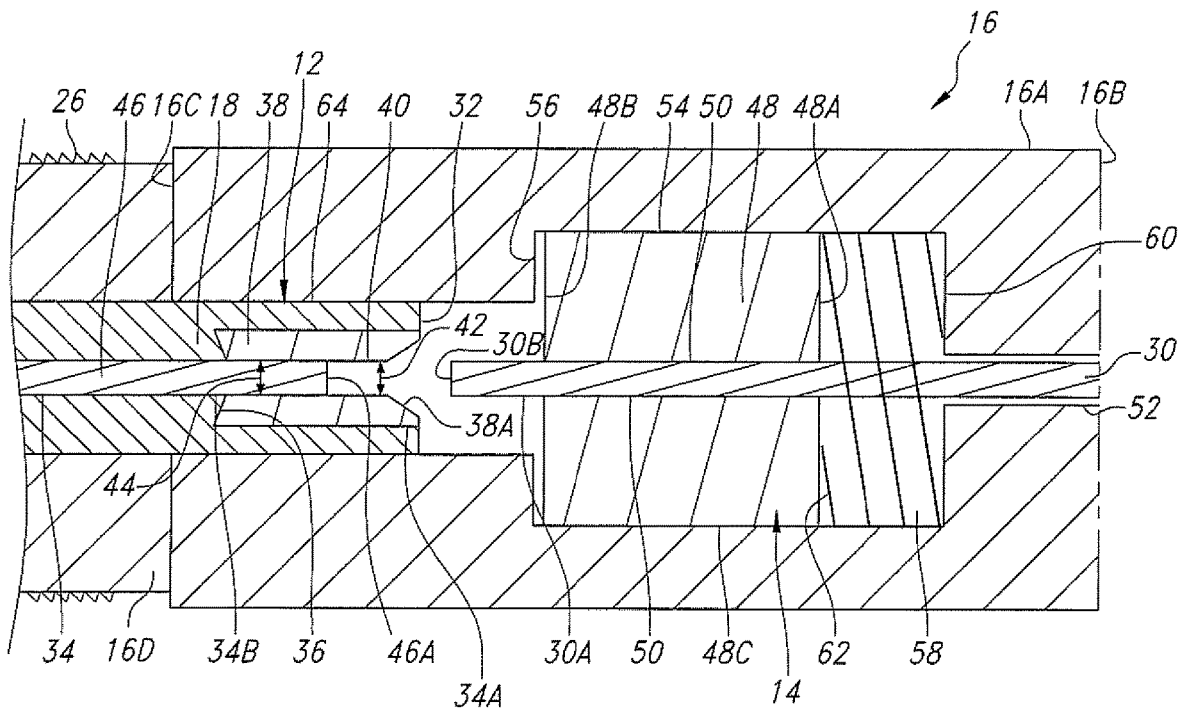
FIG. 3 is a partial cross-sectional view of the guidewire assembly 12 shown in FIG. 1 comprising a guidewire 18 supporting distal ferrule 38 and a distal optical fiber 46 moving into a distal portion 64 of an opening in the optical connector 16 shown in FIG. 2.
Figure 4:
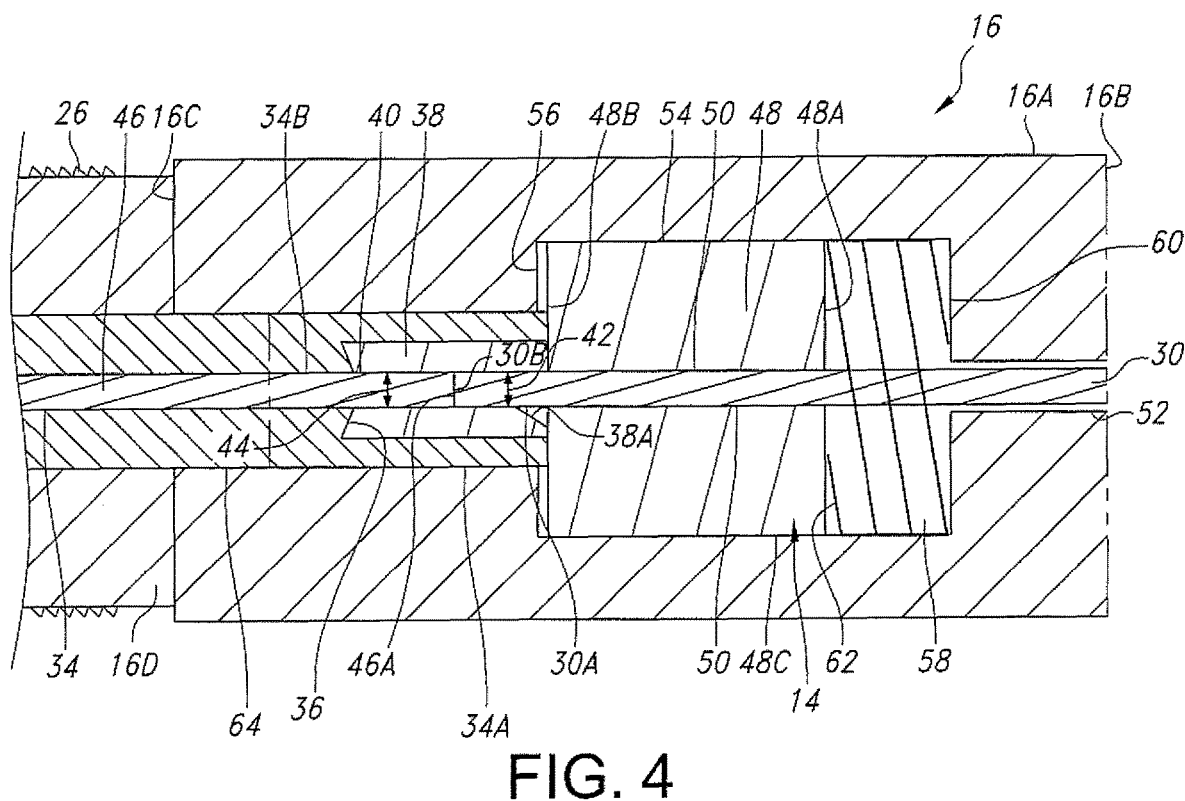
FIG. 4 is a partial cross-section view of the guidewire assembly 12 shown in FIG. 3 after having been moved proximally so that the proximal optical fiber 30 of the proximal assembly 14 mates with the distal optical fiber 46 in the distal ferrule 38 supported by the guidewire 18.

As particularly shown in FIG. 3, the guidewire lumen 34 comprises a guidewire lumen proximal portion 34A that extends distally to a step 36. A guidewire lumen distal portion 34B extends from the step 36 toward the distal end of the guidewire. In the embodiment of the present guidewire system 10 illustrated in the drawings, the guidewire lumen proximal portion 34A has a greater diameter than the guidewire lumen distal portion 34B.

A distal ferrule 38 is received in the guidewire lumen proximal portion 34A. The distal ferrule 38 has a beveled or flared proximal end 38A leading to a distal ferrule opening 40 which, with the distal ferrule residing in the guidewire lumen proximal portion 34A, is in open communication with the guidewire lumen distal portion 34B. Preferably, the inner diameter 42 of the distal ferrule opening 40 and the inner diameter 44 of the guidewire lumen distal portion 34B are substantially similar.

In an exemplary embodiment, the distal ferrule 38 has a length of about 5 mm to about 10 mm as measured from its proximal end at the flare 38A to the step 36, and the flare 38A has a length of about 0.5 mm to about 1.5 mm. The proximal and distal optical fibers 30, 46 typically range in diameter from about 30 µm±2 µm to about 200 µm±2 µm, preferably about 125 µm±2 µm. Consequently, the inner diameter 42 of the distal ferrule opening 40 ranges from about 32 µm±1 µm to about 202 µm±1 µm, preferably from about 0.125 mm±1 µm to about 0.128 mm±1 µm. This range leaves enough room for the outer diameter of the proximal optical fiber 30 and the outer diameter of the distal optical fiber 46 to fit into the inner diameter 42 of the distal ferrule opening 40.

Figure 8:
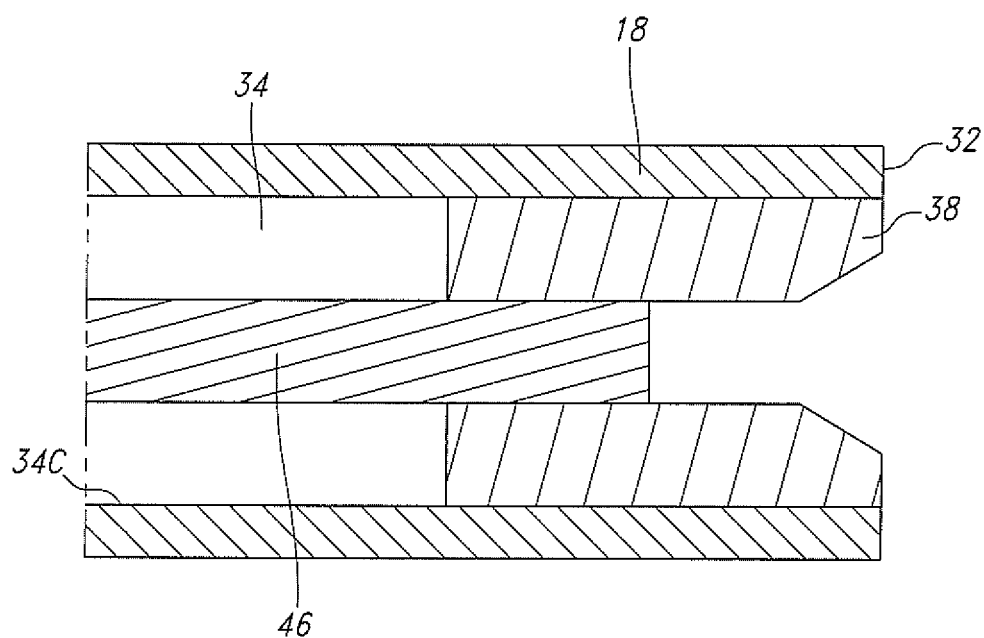
FIG. 8 is a partial cross-sectional drawing showing an alternate configuration for the distal ferrule 38 mounted in the lumen 34 extending through the guidewire 18.

In another embodiment of the present catheter system 10 shown in FIG. 8, the guidewire lumen 34 has the same diameter along its length. This means that the step 36 between the proximal and distal guidewire lumen portions 34A and 34B does not exist. Instead, the inner surface 34C of the guidewire lumen 34 is of substantially the same diameter extending from the guidewire proximal open end 32 to the distal end of the guidewire lumen. The distal ferrule 38 resides in a proximal portion of the guidewire 18 and has an opening that steps down to the inner surface 34C of the guidewire lumen 34.

A distal optical fiber 46 is received in the guidewire lumen 34 and the opening 40 in the distal ferrule 38. Preferably, a proximal end 46A of the distal optical fiber 46 resides part-way along the distance from the flared proximal end 38A of the distal ferrule opening 40 to the step 36. This is an important aspect of the present invention as a proximal portion of the distal ferrule opening 40 extending from the proximal end 46A of the distal optical fiber 46 is unoccupied by the distal optical fiber.

For example, if the distal ferrule 38 has a length of about 5 mm, the proximal end 46A of the distal optical fiber 46 occupies about 3.5 mm of that length, leaving about a 1.5 mm proximal portion of the distal ferrule opening 40 unoccupied. In another exemplary embodiment, if the distal ferrule 38 has a length of about 10 mm, the proximal end 46A of the distal optical fiber 46 occupies about 8.5 mm of that length, leaving about a 1.5 mm proximal portion of the distal ferrule opening 40 unoccupied. According to the present invention, unoccupied lengths for the proximal portion of the distal ferrule opening 40 ranging from about 1 mm to about 3 mm are contemplated.

The proximal assembly 14 comprises a generally cylindrically-shaped proximal ferrule 48 having a proximal ferrule opening 50 extending to a proximal ferrule proximal end wall 48A and a proximal ferrule distal end wall 48B. The proximal ferrule proximal and distal end walls 48A, 48B meet a generally cylindrically-shaped outer sidewall 48C.

The proximal optical fiber 30 is received in the opening 50 of the proximal ferrule 48. The proximal optical fiber 30 extends from its proximal end, which is detachably connectable to the light source 22 and reflected light receiver 24 (FIG. 1), to a distal portion 30A having a distal end 30B. The distal portion 30A of the proximal optical fiber 30 extends outwardly beyond the proximal ferrule distal end wall 48B. Preferably this distance ranges from about 1.5 mm to about 3.5 mm. This distance is longer than the unoccupied length for the proximal portion of the distal ferrule opening 40 ranging from about 1 mm to about 3 mm described above to ensure contact between the distal end 30B of the distal portion 30A of the proximal optical fiber 30 and the proximal end 46A of the distal optical fiber 46.

In an exemplary embodiment, the optical connector 16 has a cylindrically-shaped outer sidewall 16A meeting a connector proximal end wall 16B and a connector distal end wall 16C. Depending on the specific procedure that the guidewire system 10 is designed to support, however, the optical connector 16 could have a cuboid or prism shape or be shaped as a hand grip. The optical connector 16 also has a neck 16D that is connected to the distal end wall 16C. The distally extending connector neck 16D is provided with threads 26.

The connector opening has three sections of different diameters. A connector opening proximal portion 52 extends distally from the connector proximal end wall 16B to meet a connector opening intermediate portion 54. The connector opening proximal portion 52 has a first diameter that is somewhat greater than that of the proximal optical fiber 52 residing therein. The connector opening intermediate portion 54 has a second diameter that is sized to receive the proximal ferrule 48 in a sliding relationship.

In that respect, another important aspect of the present invention is that the connector opening intermediate portion 54 has a length that is longer than that of the proximal ferrule 48. With the proximal ferrule 48 received in the connector opening intermediate portion 54, abutting or proximate a distal step 56, a space 58 exists between the proximal ferrule 48 and a proximal step 60 where the connector opening intermediate portion 54 transitions or meets the connector opening proximal portion 52. This space 58 is occupied by a coil spring 62.

The distal step 56 in the optical connector 16 transitions or meets a connector opening distal portion 64 that extends to the distal end wall 16C and through the connector neck 16D. The connector opening distal portion 64 has a third diameter that is sized to receive the guidewire 18 in a sliding relationship with the guidewire supporting the distal ferrule 38 and the proximal end 46A of the distal optical fiber 46.

While not shown in the drawings, the optical connector 16 is a splittable member that is separable into two substantially similar or equal halves. When separated, the proximal assembly 14 can be moved into an open half of the connector opening intermediate portion 54. First, however, with the proximal optical fiber 30 residing in the opening 50 of the proximal ferrule 48, the spring 62 is moved over the proximal end thereof and slid along the optical fiber until the spring abuts the proximal ferrule 48. The proximal portion (not numbered) of the proximal optical fiber 30 extends outwardly from the proximal ferrule proximal end wall 48A for subsequent connection to a proximal interrogation system, for example an optical interrogation system comprising a light source, a light detector, and associate equipment. The proximal ferrule 48 supporting the proximal optical fiber 30 is then nested in an open half of the connector opening intermediate portion 54 with the proximal optical fiber 30 extending proximally through the connector opening proximal portion 52. In this position, the distal portion 30A of the proximal optical fiber 30 extends outwardly and distally a relatively short distance from the proximal ferrule distal end wall 48B and into the connector opening distal portion 64. The spring 62 now resides in the space 58 between the proximal ferrule 48 and the proximal step 60 where the connector opening intermediate portion 54 meets the connector opening proximal portion 52.

The other half of the optical connector 16 is then mated with the half nesting the proximal ferrule 48 and the proximal optical fiber 30 and the spring 62. The halves are then secured together, for example using threaded fasteners, to thereby provide the assembled optical connector 16.

Figure 5:
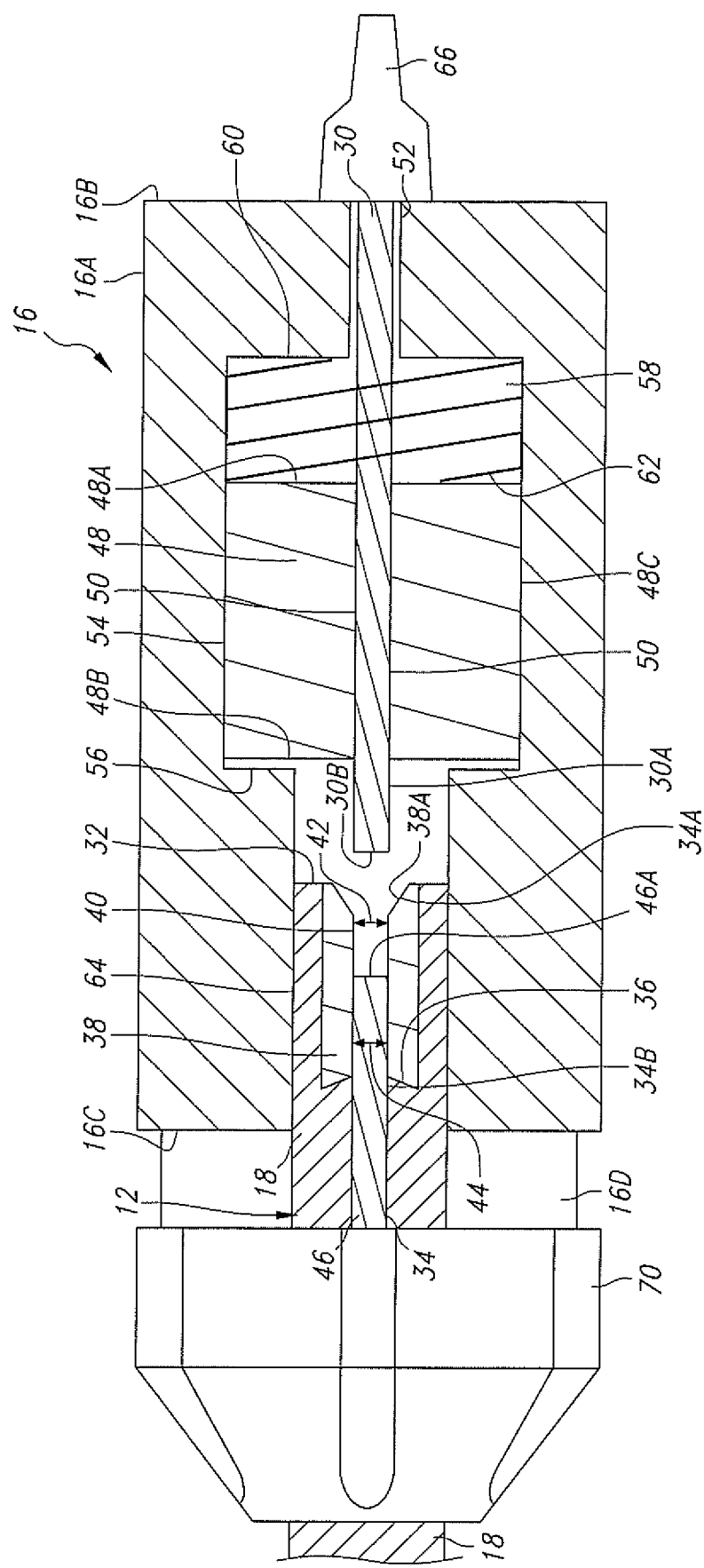
FIG. 5 is a partial cross-sectional view of the guidewire assembly 12 shown in FIGS. 2 and 3 with the optical connector 16 provided with a collet 70.
Figure 6:
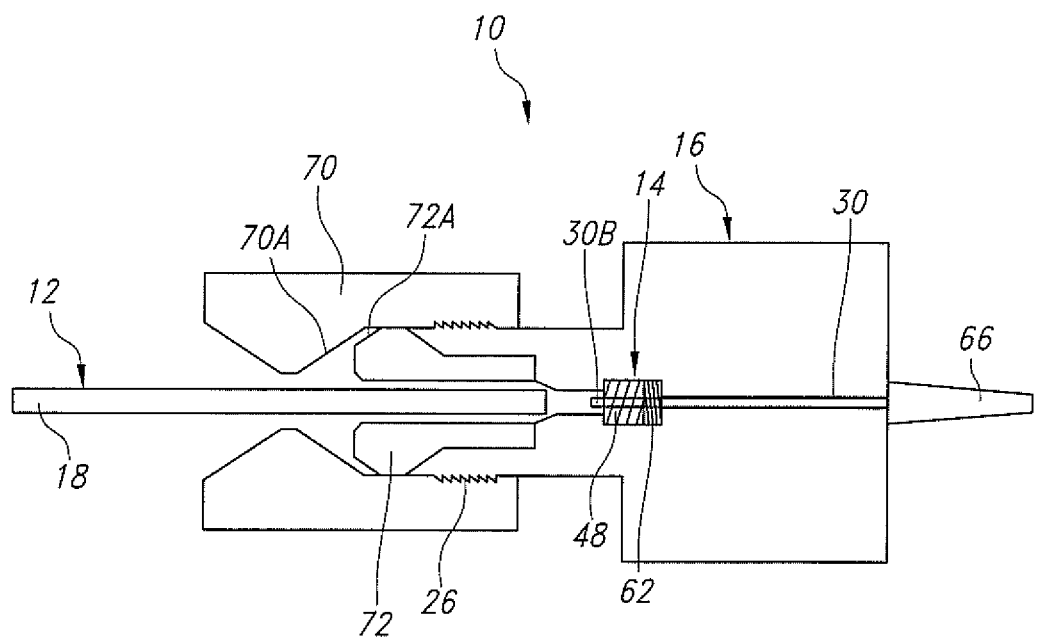
FIG. 6 is a schematic view of the guidewire system 10 illustrated in FIG. 1 and showing the guidewire assembly 12 moving into the opening in the optical connector 16 as shown in FIG. 5 with a locking collet 70 and tapered collar 72 assembly supported on the optical connector 16.
Figure 7:
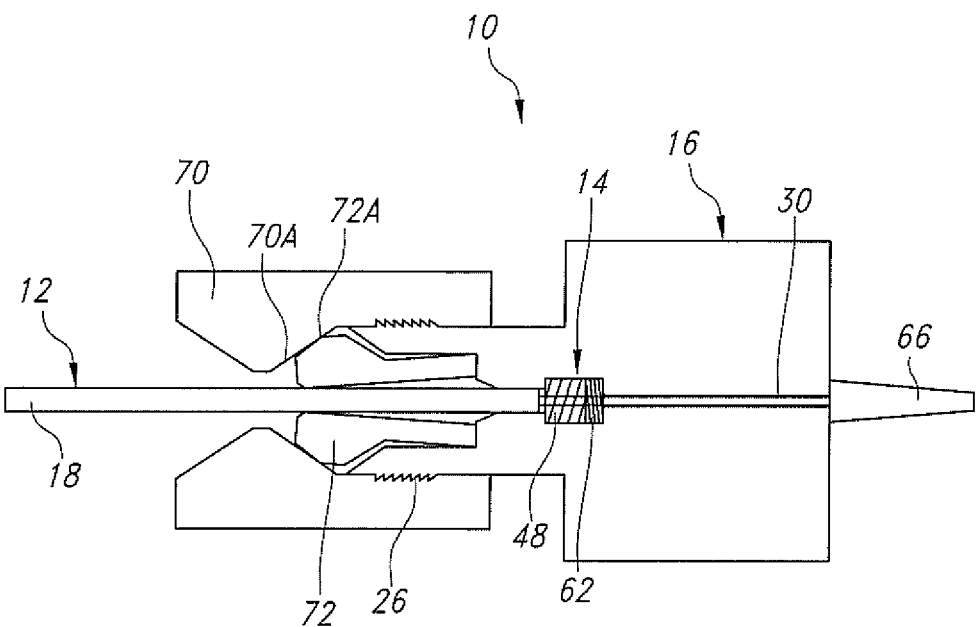
FIG. 7 is a schematic view of the guidewire system 10 shown in FIG. 6 but with the locking collet 70 and tapered collar 72 assembly having tightened onto the optical connector 16 to secure the guidewire assembly 12 in place inside the optical connector 16.

As shown in FIGS. 5 to 7, the proximal optical fiber 30 is provided with a strain relief sleeve 66 abutting the proximal end wall 16B of the optical connector. The strain-relief sleeve 66 adds support to the proximal optical fiber 30 and helps prevent wear of its protective sheath (not shown).

As further shown in FIGS. 5 to 7, the distally extending connector neck 68 supports a locking collet 70 and an intermediate tapered collar 72 assembly. Preferably, the connector neck 68 and the collet 70 are provided with matching threads so that they are in a threaded engagement with each other.

Figure 2:
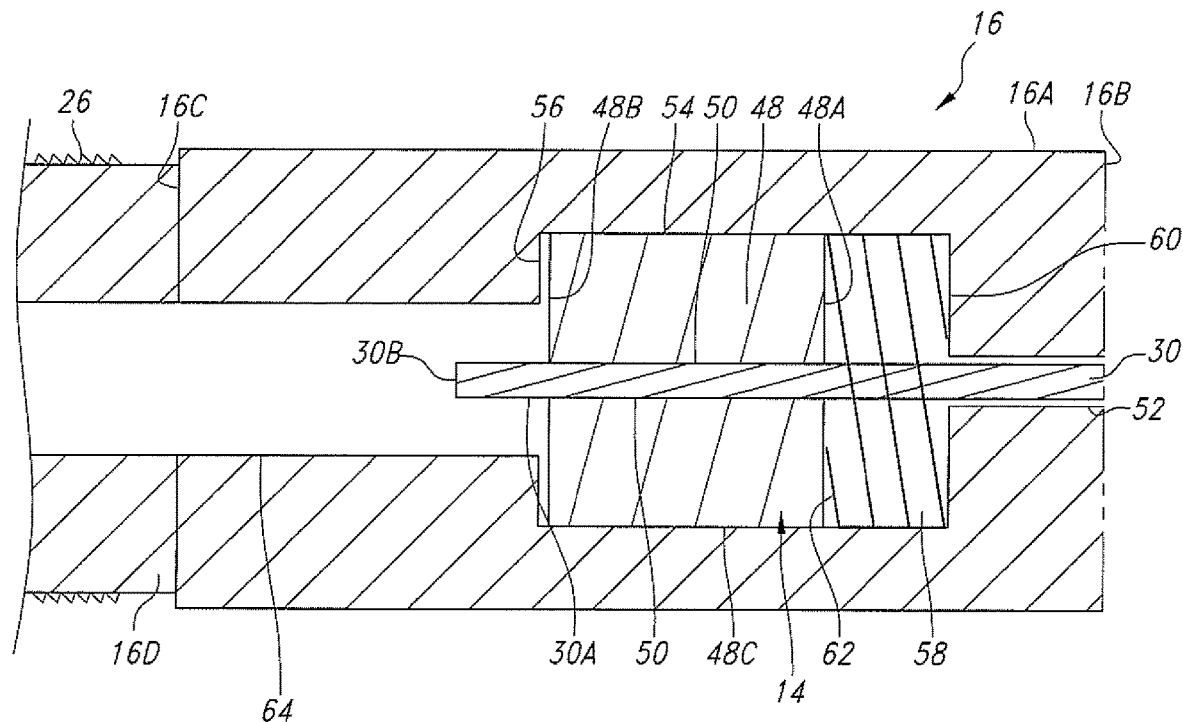
FIG. 2 is a partial cross-sectional view of a proximal assembly 14 comprising a proximal ferrule 48 supporting a proximal optical fiber 30 and a coil spring 62 housed in the optical connector 16 of FIG. 1.

In use, with the optical connector 16 supporting the proximal assembly 14 including the proximal optical fiber 30 as shown in FIG. 2, the proximal end of the guidewire 18 is inserted through the collet 70 and the connector neck 16D and into the distal portion 64 of the connector opening. As shown in FIG. 5, the guidewire 18 supporting the distal ferrule 38 and the distal optical fiber 46 is moved through the connector opening distal portion 64 until the distal portion 30A of the proximal optical fiber 30 extending outwardly beyond the proximal ferrule distal end wall 48B is fully received in the previously unoccupied proximal portion of the distal ferrule opening 40. The distal end of the proximal optical fiber 30 is now optically connected to the proximal end of the distal optical fiber 46. Moreover, when the proximal and distal optical fibers 30, 46 meet in the distal ferrule opening 40, they automatically self-align as the diameter of that opening through the distal ferrule supported by the guidewire is consistent throughout its length.

To help ensure that the proximal and distal optical fibers 30, 46 are not damaged as they contact each other, the previously described coil spring 62 provides a degree of biasing resistance that permits proximal translation of the proximal ferrule 48. This biased proximal movement is for a relatively short distance and helps absorb any potentially damaging forces that might occur as the distal optical fiber 46 moves into contact with the proximal optical fiber 30. Then, when the physician or practitioner feels resistance from the spring-loaded proximal ferrule 48 in the optical connector 16, the guidewire 18 is clamped into position by twisting the collet 70 onto the connector neck 68. As schematically shown in FIG. 6, the collet 70 has an internal cam surface 70A that rams against a matching cam surface 72A of the tapered collar 72. This movement causes the tapered collar 72 to tighten against the ferrule (FIG. 7) to thereby lock the ferrule assembly 12 in position.

Thus, a guidewire system 10 of the present invention enables a diagnostic or therapeutic instrument, for example a catheter, to be loaded onto the proximal open end 32 of the guidewire 18 so that a diagnostic or therapeutic instrument can travel over the guidewire to a point of interest in the vasculature of a patient. This is made possible by the optical connector 16 which provides for readily and reliably optically connecting the proximal optical fiber 30 to the distal optical fiber 46 supported by the guidewire 18. The optical connector 16 allows the guidewire 18 and its distal optical fiber 46 to be inserted into the patient's vasculature so that a catheter or other diagnostic or therapeutic instrument can be moved over the guidewire and into the vasculature. Then, with the diagnostic or therapeutic instrument received over the guidewire 18, the optical connector 16 enables the guidewire 18 and its distal optical fiber 46 to be optically connected to the proximal optical fiber 30. This connection is made with the guidewire 18 having been inserted into the vasculature at any rotational angle without significant power loss across the optical connector 16.

It is appreciated that various modifications to the inventive concepts described herein may be apparent to those of ordinary skill in the art without departing from the spirit and scope of the present invention as defined by the appended claims.

What is claimed is:
1. A guidewire system, comprising:
a) a guidewire assembly, comprising:
   i) a guidewire comprising a guidewire proximal portion spaced from a guidewire distal portion, wherein the guidewire has a lumen that extends from a guidewire lumen proximal portion having a guidewire lumen proximal open end residing in the guidewire proximal portion to a guidewire lumen distal open end residing in the guidewire distal portion;
   ii) a distal ferrule comprising a distal ferrule opening having an open length extending to a distal ferrule proximal open end and a distal ferrule distal open end, wherein the distal ferrule resides in the guidewire lumen proximal portion with the distal ferrule opening being in open communication with the guidewire lumen; and
   iii) a distal optical fiber extending from a distal optical fiber proximal portion having a distal optical fiber proximal end to a distal optical fiber distal end, wherein the distal optical fiber proximal portion resides in the distal ferrule opening with a proximal portion of the open length of the distal ferrule opening being unoccupied by the distal optical fiber;
b) a proximal assembly, comprising:
   i) a proximal ferrule having a proximal ferrule opening extending to a proximal ferrule proximal end wall and a proximal ferrule distal end wall; and
   ii) a proximal optical fiber extending from a proximal optical fiber proximal end to a proximal optical fiber distal portion having a proximal optical fiber distal end; and
c) an optical connector comprising:
   i) an optical connector opening extending to an optical connector proximal open end and an optical connector distal open end, wherein the optical connector opening has an enlarged diameter open portion intermediate the proximal and distal open ends, and wherein the proximal ferrule of the proximal assembly resides in the enlarged diameter open portion of the optical connector; and
   ii) a coil spring residing in the enlarged diameter open portion of the optical connector,
   iii) wherein the proximal optical fiber extends through the optical connector proximal open end, the coil spring, and the proximal ferrule opening with the coil spring abutting the proximal ferrule proximal end wall, and wherein the distal portion of the proximal optical fiber extends distally outwardly beyond the proximal ferrule distal end wall but is spaced proximally from the optical connector distal open end,
d) wherein the guidewire assembly is movable in a proximal direction into the optical connector distal open end and along the optical connector opening until the distally extending distal portion of the proximal optical fiber is received in the unoccupied proximal portion of the open length of the distal ferrule opening to thereby optically connect the distal end of the proximal optical fiber to the proximal end of the distal optical fiber as the coil spring biases against proximal movement of the proximal ferrule along the enlarged diameter open portion of the optical connector, and e) wherein the guidewire assembly is then movable in a distal direction to move the distal ferrule distally along the optical connector opening with the proximal optical fiber no longer residing in the proximal portion of the open length of the distal ferrule opening to optically disconnect the distal end of the proximal optical fiber from the proximal end of the distal optical fiber so that when the distal ferrule residing in the guidewire lumen proximal portion is moved distally out of the optical connector distal open end, the guidewire assembly is disconnected from the optical connector and the proximal assembly.

2. The guidewire system of claim 1, wherein the optical connector is splittable so that the proximal ferrule and the proximal optical fiber are movable into and out of the enlarged diameter open portion of the optical connector opening.

3. The guidewire system of claim 1, wherein the distal ferrule of the guidewire assembly is flared outwardly and proximally at the distal ferrule proximal open end.

4. The guidewire system of claim 1, wherein the guidewire lumen proximate the guidewire lumen proximal open end has an enlarged guidewire lumen portion, and wherein the distal ferrule resides in the enlarged guidewire lumen portion.

5. The guidewire system of claim 1, wherein the guidewire lumen has the same diameter along its length, and wherein the distal ferrule resides in the guidewire lumen proximate the guidewire lumen proximal open end.

6. The guidewire system of claim 1, further comprising a locking collet and collar assembly, wherein the optical connector comprises an extending neck that is threadingly mateable to the locking collet and collar assembly to selectively lock and unlock the guidewire in the optical connector.

7. The guidewire system of claim 1, wherein the unoccupied proximal portion of the open length of the distal ferrule opening ranges from about 1 mm to about 3 mm, and wherein the distal portion of the proximal optical fiber extends distally outwardly beyond the proximal ferrule distal end wall for a distance ranging from about 1.5 mm to about 3.5 mm.

8. The guidewire system of claim 1, wherein the inner diameter of the distal ferrule opening ranges from about 32 µm±1 µm to about 202 µm±1 µm.

9. The guidewire system of claim 1, wherein the proximal optical fiber proximal end is configured to be optically connectable to a light source.

10. A guidewire assembly, comprising:
a) a guidewire comprising a guidewire proximal portion spaced from a guidewire distal portion, wherein the guidewire has a guidewire lumen that extends from a guidewire lumen proximal open end residing in the guidewire proximal portion to a guidewire lumen distal open end residing in the guidewire distal portion;
b) a ferrule having a ferrule length extending from a ferrule proximal end to a ferrule distal end, the ferrule comprising a ferrule opening having a ferrule open length coinciding with the ferrule length and extending to a ferrule opening proximal open end at the ferrule proximal end to a ferrule opening distal open end at the ferrule distal end, wherein the entire ferrule length resides in the guidewire lumen proximal portion with the ferrule opening being in open communication with the guidewire lumen; and c) an optical fiber extending from an optical fiber proximal portion having an optical fiber proximal end to an optical fiber distal end, wherein the optical fiber resides in the guidewire lumen with the optical fiber proximal portion residing in the ferrule opening, and wherein a proximal portion of the ferrule open length is unoccupied by the optical fiber.

11. The guidewire assembly of claim 10, wherein the unoccupied proximal portion of the ferrule open length ranges from about 1 mm to about 3 mm.

12. The guidewire assembly of claim 10, wherein the ferrule of the guidewire assembly is flared outwardly and proximally at the ferrule opening proximal open end.

13. The guidewire assembly of claim 10, wherein the guidewire lumen proximate the guidewire lumen proximal open end has an enlarged guidewire lumen portion, and wherein the entire ferrule length resides in the enlarged guidewire lumen portion.

14. The guidewire assembly of claim 10, wherein the guidewire lumen has the same diameter along its length, and wherein the entire ferrule length resides in the guidewire lumen proximate the guidewire lumen proximal open end.

15. The guidewire assembly of claim 10, wherein an inner diameter of the ferrule opening ranges from about 32 µm±1 µm to about 202 µm±1 µm.

16. A guidewire system, comprising:
a) a guidewire assembly, comprising:
i) a guidewire comprising a guidewire proximal portion spaced from a guidewire distal portion, wherein the guidewire has a lumen that extends from a guidewire lumen proximal portion having a guidewire lumen proximal open end residing in the guidewire proximal portion to a guidewire lumen distal open end residing in the guidewire distal portion;
ii) a distal ferrule comprising a distal ferrule opening having an open length extending to a distal ferrule proximal open end and a distal ferrule distal open end, wherein the distal ferrule resides in the guidewire lumen proximal portion with the distal ferrule opening being in open communication with the guidewire lumen; and
iii) a distal optical fiber extending from a distal optical fiber proximal portion having a distal optical fiber proximal end to a distal optical fiber distal end, wherein the distal optical fiber proximal portion resides in the distal ferrule opening with a proximal portion of the open length of the distal ferrule opening being unoccupied by the distal optical fiber;
b) a proximal assembly, comprising:
i) a proximal ferrule having a proximal ferrule opening extending to a proximal ferrule proximal end wall and a proximal ferrule distal end wall; and
ii) a proximal optical fiber extending from a proximal optical fiber proximal end to a proximal optical fiber distal portion having a proximal optical fiber distal end; and
c) an optical connector comprising:
i) an optical connector opening extending to an optical connector proximal open end and an optical connector distal open end, wherein the proximal ferrule of the proximal assembly resides in the optical connector opening with the proximal optical fiber extending through the optical connector proximal open end and the proximal ferrule opening,
ii) wherein the distal portion of the proximal optical fiber extends distally outwardly beyond the proximal ferrule distal end wall but is spaced proximally from the optical connector distal open end, d) wherein the guidewire assembly is movable in a proximal direction into the optical connector distal open end and along the optical connector opening until the distally extending distal portion of the proximal optical fiber is received in the unoccupied proximal portion of the open length of the distal ferrule opening to thereby optically connect the distal end of the proximal optical fiber to the proximal end of the distal optical fiber, and e) wherein the guidewire assembly is then movable in a distal direction to move the distal ferrule distally along the optical connector opening with the proximal optical fiber no longer residing in the proximal portion of the open length of the distal ferrule opening to optically disconnect the distal end of the proximal optical fiber from the proximal end of the distal optical fiber so that when the distal ferrule residing in the guidewire lumen proximal portion is moved distally out of the optical connector distal open end, the guidewire assembly is disconnected from the optical connector and the proximal assembly.

17. The guidewire system of claim 16, wherein the optical connector is splittable so that the proximal ferrule and the proximal optical fiber are movable into and out of the optical connector opening.

18. The guidewire system of claim 16, wherein the guidewire lumen proximate the guidewire lumen proximal open end has an enlarged guidewire lumen portion, and wherein the distal ferrule resides in the enlarged guidewire lumen portion.

19. The guidewire system of claim 16, further comprising a locking collet and collar assembly, wherein the optical connector comprises an extending neck that is threadingly mateable to the locking collet and collar assembly to selectively lock and unlock the guidewire in the optical connector.

20. The guidewire system of claim 16, wherein the proximal optical fiber proximal end is configured to be optically connectable to a light source.

* * * * *